(12) United States Patent
Zhang et al.

(10) Patent No.: US 9,241,966 B1
(45) Date of Patent: Jan. 26, 2016

(54) EXTERNAL-USE TRADITIONAL CHINESE MEDICINE FOR ICHTHYOSIS AND XERODERMIA, AND PREPARATION METHOD THEREOF

(71) Applicant: Sen Tong, Chaoyang District, Beijing (CN)

(72) Inventors: Jian Zhang, Beijing (CN); Sen Tong, Beijing (CN)

(73) Assignee: Sen Tong (CN)

( * ) Notice: Subject to any disclaimer, the term of this patent is extended or adjusted under 35 U.S.C. 154(b) by 0 days.

(21) Appl. No.: 14/336,255

(22) Filed: Jul. 21, 2014

(51) Int. Cl.
| | |
|---|---|
| *A61K 36/00* | (2006.01) |
| *A61K 36/886* | (2006.01) |
| *A61K 36/258* | (2006.01) |
| *A61K 36/75* | (2006.01) |
| *A61K 36/28* | (2006.01) |
| *A61K 36/736* | (2006.01) |
| *A61K 36/481* | (2006.01) |
| *A61K 45/06* | (2006.01) |

(52) U.S. Cl.
CPC .............. *A61K 36/886* (2013.01); *A61K 36/00* (2013.01); *A61K 36/258* (2013.01); *A61K 36/28* (2013.01); *A61K 36/481* (2013.01); *A61K 36/736* (2013.01); *A61K 36/75* (2013.01); *A61K 45/06* (2013.01)

(58) Field of Classification Search
None
See application file for complete search history.

*Primary Examiner* — Qiuwen Mi
(74) *Attorney, Agent, or Firm* — Harness, Dickey & Pierce, P.L.C.

(57) ABSTRACT

An external-use curing and nursing traditional Chinese medicine for ichthyosis and xerodermia include, in parts by weight, for curing: 6-10 Cortex Dictamni, 5-8 Herba Lycopodii, 3-8 Flos Carthami, 3-8 Herba speranskiae tuberculatae, 6-10 Herba Menthae, 4-8 Folium Artemisiae Argyi, 3-6 GONGGUI, 3-6 Fructus Kochiae, 3-6 Cortex erythrinae, 3-6 Herba Artemisiae, 3-6 Ramulus Mori, 3-6 Bletilla striata, 3-8 Radix Paeoniae Rubra, 3-6 Rhizoma Atractylodis, 3-6 Asarum sieboldi, 2-4 Herba Leonuri, 3-5 Radix Ginseng Rubra, and 4-8 Radix Bupleuri; and include, in parts by weight, for nursing: 3-6 Rehmannia glutinosa Libosch, 3-6 Rehmannia glutinosa, 3-6 Paeonia suffruticosa Andr., 3-5 Alisma plantago aquatica, 3-8 Ophiopogon japonicus, 3-8 aloes, 10-30 Astragalus membranaceus, 3-5 Poria cocos, 5-14 FRUCTUS CORNI, 5-14 Rhizoma Dioscoreae, 3-6 peach kernel, 3-6 tremella, and 1-3 Panax. It is convenient to use, pain free, no side effect, no anti-medicine reaction is produced, and it operates quickly and has significant therapeutic effect.

24 Claims, 2 Drawing Sheets

EXTERNAL-USE TRADITIONAL CHINESE MEDICINE FOR ICHTHYOSIS AND XERODERMIA, AND PREPARATION METHOD THEREOF

TECHNICAL FIELD

The present invention relates to the pharmaceutical field, and particularly to external-use traditional Chinese medicine for ichthyosis and xerodermia and the preparation method thereof.

BACKGROUND

Ichthyosis is a group of hereditary keratinization disordered dermatosis, which is referred to as "pityriasis or squamous and dry skin" in traditional Chinese medical science. In the traditional Chinese medical science, it is considered that the cause is mainly congenital deficiency of natural endowment. Congenital deficiency of kidney-essence causes spleen and lung yin deficiency arriving, body and skin missing nutrition, i.e. skin of snakeskin shape and scale like appears. Based on syndrome differentiation of zang-fu viscera, the root of ichthyosis lies in kidney, the origin thereof lies in spleen, and the symptom appears in lung. If a person has weak natural endowment, i.e, both the kidney and the spleen being deficiency congenitally, the kidney-essence being weak and few, and the spleen being unable to transportation and transformation, then the meridians are sluggish, qi and blood are stasis, and the skin cannot be fostered from the essence and blood, characterized as multifocal skin of snakeskin shape and scale like of the whole body. Ichthyosis is mainly characterized as xerosis cutis, associated along with fish scale desquamation. This disease primarily onsets during childhood, mainly characterized as the skin on side of the four limbs or torso portion dry and coarse, accompanied by rhombus or polygonal scales, with appearance as fish scale like or snakeskin shape. The disease gets worse in cold and dry season and better in warm and humid season. The disease is easy to recur. The hereditary factors cause epithelial cells proliferation and differentiation abnormal, leading to cells proliferation increased and (or) cells desquamation decreased.

The current situation of curing and nursing of ichthyosis is as follows:

1. oral drugs: the oral manner was often adopted in the past, and however the side effect of oral drugs is significant, for example, heavy dose of vitamin A causes serious side effect, making both doctors and patients awed by the sight even from distance. Even the side effect of the traditional Chinese herbal medicine is lower, if it is taken for a long term, more side effect could also occur due to the accumulation of heavy dose of drug, therefore generally it is not suggested to undergo oral curing and externally nursing for a long term.

2. external-use method: at present, there are methods such as fumigating, laser etc, but all these methods cannot prevent recurrence, and prophylaxis and treatment are not carried out by a same method, resulting in recurrence on many people.

SUMMARY OF THE INVENTION

The object of the present invention is to provide external-use traditional Chinese medicine for ichthyosis and xerodermia so as to solve the above problems.

The external-use traditional Chinese medicine for ichthyosis and xerodermia provided by the present invention comprises external-use curing traditional Chinese medicine and external-use nursing traditional Chinese medicine, wherein parts by weight are as follows:

raw materials of the external-use curing traditional Chinese medicine comprises: Cortex Dictamni in 6-10 parts, Herba Lycopodii 5-8 in parts, Flos Carthami in 3-8 parts, Herba speranskiae tuberculatae in 3-8 parts, Herba Menthae in 6-10 parts, Folium Artemisiae Argyi in 4-8 parts, GONGGUI in 3-6 parts, Fructus Kochiae in 3-6 parts, Cortex erythrinae in 3-6 parts, Herba Artemisiae in 3-6 parts, Ramulus Mori in 3-6 parts, Bletilla striata in 3-6 parts, Radix Paeoniae Rubra in 3-8 parts, Rhizoma Atractylodis in 3-6 parts, Asarum sieboldi in 3-6 parts, Herba Leonuri in 2-4 parts, Radix Ginseng Rubra in 3-5 parts, and Radix Bupleuri in 4-8 parts; and raw materials of the external-use nursing traditional Chinese medicine comprises: Rehmannia glutinosa Libosch in 3-6 parts, Rehmannia glutinosa in 3-6 parts, Paeonia suffruticosa Andr. in 3-6 parts, Alisma plantago aquatica in 3-5 parts, Ophiopogon japonicus in 3-8 parts, aloes in 3-8 parts, Astragalus membranaceus in 10-30 parts, Poria cocos in 3-5 parts, FRUCTUS CORNI in 5-14 parts, Rhizoma Dioscoreae in 5-14 parts, peach kernel in 3-6 parts, tremella in 3-6 parts, and Panax in 1-3 parts.

After a series of experiments are performed, the inventor has made compatibility between different medical materials, and finally determines that Cortex Dictamni, Herba Lycopodii, Flos Carthami, Herba speranskiae tuberculatae, Herba Menthae, Folium Artemisiae Argyi, GONGGUI, Fructus Kochiae, Cortex erythrinae, Herba Artemisiae, Ramulus Mori, Bletilla striata, Radix Paeoniae Rubra, Rhizoma Atractylodis, Asarum sieboldi, Herba Leonuri, Radix Ginseng Rubra and Radix Bupleuri are selected as the raw materials of the external-use curing traditional Chinese medicine. After the above various medical materials are mixed according to the following parts by weight: Cortex Dictamni in 6-10 parts, Herba Lycopodii 5-8 in parts, Flos Carthami in 3-8 parts, Herba speranskiae tuberculatae in 3-8 parts, Herba Menthae in 6-10 parts, Folium Artemisiae Argyi in 4-8 parts, GONGGUI in 3-6 parts, Fructus Kochiae in 3-6 parts, Cortex erythrinae in 3-6 parts, Herba Artemisiae in 3-6 parts, Ramulus Mori in 3-6 parts, Bletilla striata in 3-6 parts, Radix Paeoniae Rubra in 3-8 parts, Rhizoma Atractylodis in 3-6 parts, Asarum sieboldi in 3-6 parts, Herba Leonuri in 2-4 parts, Radix Ginseng Rubra in 3-5 parts, and Radix Bupleuri in 4-8 parts, the active ingredients of the various medicinal materials produce positive synergy. This external-use curing traditional Chinese medicine can not only quickly remove scales, but also promote the body to release free amino acid, maintaining dynamic equilibrium of moisture of the skin, playing functions of dredging pores, lubricating the skin, softening horniness, strengthening metabolism and absorption of the skin, to reach the purpose of eliminating focus from internal of the body.

Rehmannia glutinosa Libosch, Rehmannia glutinosa, Paeonia suffruticosa Andr., Alisma plantago aquatica, Ophiopogon japonicus, aloes, Astragalus membranaceus, Poria cocos, FRUCTUS CORNI, Rhizoma Dioscoreae, peach kernel, tremella and Panax are selected as the raw materials of the external-use nursing traditional Chinese medicine. After the above various medical materials are mixed according to the following parts by weight: Rehmannia glutinosa Libosch in 3-6 parts, Rehmannia glutinosa in 3-6 parts, Paeonia suffruticosa Andr. in 3-6 parts, Alisma plantago aquatica in 3-5 parts, Ophiopogon japonicus in 3-8 parts, aloes in 3-8 parts, Astragalus membranaceus in 10-30 parts, Poria cocos in 3-5 parts, FRUCTUS CORNI in 5-14 parts, Rhizoma Dioscoreae in 5-14 parts, peach kernel in 3-6 parts, tremella in 3-6 parts, and Panax in 1-3 parts, the active ingredients of the various medicinal materials produce positive synergy. The external-use nursing traditional Chinese medicine has efficacy of continuously fostering the skin cell, activating immunologic function of the skin, and balancing the metabolism of free amino acid in epidermis, and recovering normal secreting function of sebaceous glands and sweat glands.

The external-use curing traditional Chinese medicine of the present invention eliminates the focus mainly from internal of the body, while the external-use nursing traditional Chinese medicine continuously fosters the skin cell from external of the body, both being used in conjunction with features of inner and outer concurrently therapy and treating the disease in both the principal aspect and secondary aspect, and can radically solve problems of recurrence of ichthyosis, reaching the purpose of long term cure.

Preferably, the raw materials of the external-use curing traditional Chinese medicine comprise Cortex Dictamni in 7-9 parts, Herba Lycopodii 6-7 in parts, Flos Carthami in 4-6 parts, Herba speranskiae tuberculatae in 4-7 parts, Herba Menthae in 7-9 parts, Folium Artemisiae Argyi in 5-7 parts, GONGGUI in 4-5 parts, Fructus Kochiae in 4-5 parts, Cortex erythrinae in 4-5 parts, Herba Artemisiae in 4-5 parts, Ramulus Mori in 4-6 parts, Bletilla striata in 4-5 parts, Radix Paeoniae Rubra in 4-7 parts, Rhizoma Atractylodis in 4-5 parts, Asarum sieboldi in 5-6 parts, Herba Leonuri in 3-4 parts, Radix Ginseng Rubra in 4-5 parts, and Radix Bupleuri in 5-7 parts.

Preferably, the raw materials of the external-use nursing traditional Chinese medicine comprise Rehmannia glutinosa Libosch in 4-5 parts, Rehmannia glutinosa in 4-5 parts, Paeonia suffruticosa Andr. in 4-5 parts, Alisma plantago aquatica in 4-5 parts, Ophiopogon japonicus in 4-7 parts, aloes in 4-7 parts, Astragalus membranaceus in 15-25 parts, Poria cocos in 4-5 parts, FRUCTUS CORNI in 7-12 parts, Rhizoma Dioscoreae in 8-12 parts, peach kernel in 4-5 parts, tremella in 4-5 parts, and Panax in 2-3 parts.

The present invention also provides a preparation method of the external-use traditional Chinese medicine for ichthyosis and xerodermia, comprising preparation method of the external-use curing traditional Chinese medicine and preparation method of the external-use nursing traditional Chinese medicine.

The preparation method of the external-use curing traditional Chinese medicine comprises the following steps: mixing the raw materials of the external-use curing traditional Chinese medicine and packing it into an organza bag to obtain a medicine package; or the preparation method of the external-use curing traditional Chinese medicine comprises the following steps:

(1) mixing the raw materials of the external-use curing traditional Chinese medicine;

(2) after adding 25-35 L clear water, firstly boiling it with high heat, and then decocting it for 20-40 minutes with slow fire; and (3) filtering it to obtain liquid medicine.

The preparation method of the external-use nursing traditional Chinese medicine comprises the following steps: mixing and then grinding the raw materials of the external-use nursing traditional Chinese medicine, and passing it through a sieve with 100-140 meshes, to obtain the product.

The purpose of grinding the raw materials and passing it through the sieve with 100-140 meshes is to make the grain of the end product of the nursing traditional Chinese medicine with smaller size, because grain with smaller size can improve human body's absorption and bioavailability of the active ingredients of medical materials, thereby significantly improving drug effect. However, grain with too small size would increase the difficulty in grinding and the grinding time, the requirement on the equipment high and the production cost increased.

The external-use curing traditional Chinese medicine of the present invention uses Cortex Dictamni, Herba Lycopodii, Flos Carthami, Herba speranskiae tuberculatae, Herba Menthae, Folium Artemisiae Argyi, GONGGUI, Fructus Kochiae, Cortex erythrinae, Herba Artemisiae, Ramulus Mori, Bletilla striata, Radix Paeoniae Rubra, Rhizoma Atractylodis, Asarum sieboldi, Herba Leonuri, Radix Ginseng Rubra and Radix Bupleuri as the raw materials. By controlling the amount of each raw material and by improving the preparation method, the prepared external-use curing traditional Chinese medicine has extraordinary efficacy of clearing heat and detoxicating, promoting blood circulation and removing blood stasis, relieving rigidity of muscles and activating collaterals and balancing the function of zang-fu viscera. Particularly, by controlling the amount of the added clear water and the decocting time, the active ingredients of various medical materials can be sufficiently released, and the various active ingredients are supplementary to each other, producing positive synergy, and dramatically increasing the therapeutic effect.

The external-use nursing traditional Chinese medicine of the present invention uses Rehmannia glutinosa Libosch, Rehmannia glutinosa, Paeonia suffruticosa Andr., Alisma plantago aquatica, Ophiopogon japonicus, aloes, Astragalus membranaceus, Poria cocos, FRUCTUS CORNI, Rhizoma Dioscoreae, peach kernel, tremella and Panax as the raw materials. By controlling the amount of each medical material and by improving the preparation method, the prepared external-use nursing traditional Chinese medicine has extraordinary efficacy of repairing skin defects such as skin lines, drying and chapping and skin types being too stiff. Particularly, by controlling the meshes of the ground medical materials, the active ingredients of the medical materials are easy to be absorbed, improving the bioavailability, and dramatically increasing the therapeutic effect.

Preferably, in the preparation method of the external-use nursing traditional Chinese medicine, the raw materials of the external-use nursing traditional Chinese medicine are passed through a sieve with 120 meshes after being mixed and ground.

Preferably, in the step (2) of the preparation method of the external-use curing traditional Chinese medicine, the volume of the added clear water is 30 L.

Preferably, in the step (2) of the preparation method of the external-use curing traditional Chinese medicine, the decocting time is 25-35 minutes.

During the decocting, the amount of the added clear water and the decocting time must be controlled strictly, since if the amount of the added clear water is too little, and the decocting time is too short, the active ingredients of the medical materials cannot be released completely, making the component content of the active ingredients in the liquid medicine low, incapable of reaching good therapeutic effect; and if the amount of the added clear water is too much, and the decocting time is too long, a large amount of heat energy will be consumed, wasting the valuable energy.

Preferably, in the step (2) of the preparation method of the external-use curing traditional Chinese medicine, the decocting time is 30 minutes.

Preferably, vaseline and honey are added to the external-use nursing traditional Chinese medicine, mixed well to form nursing paste, wherein mass ratio of the external-use nursing traditional Chinese medicine, the vaseline and the honey is 2-3:0.5-1.5:0.5-1.5.

The amount of the added vaseline and honey is determined according to viscosity and softness of the nuring paste, and associated with water absorption of the medical materials. If the water absorption is strong, the amount of the vaseline and honey is large; if the water absorption is poor, the amount of weak water absorption is small. In practice, it is found that if the mass ratio of the external-use nursing traditional Chinese medicine and the vaseline and the honey is controlled as 2-3:0.5-1.5:0.5-1.5, the prepared nursing paste has moderate viscosity and softness, easy to be used.

Preferably, the mass ratio of the external-use nursing traditional Chinese medicine, the vaseline and the honey is 2:1:1.

Compared with the prior art, the present invention has the following beneficial effects:

The external-use curing traditional Chinese medicine of the present invention uses Cortex Dictamni, Herba Lycopodii, Flos Carthami, Herba speranskiae tuberculatae, Herba Menthae, Folium Artemisiae Argyi, GONGGUI, Fructus Kochiae, Cortex erythrinae, Herba Artemisiae, Ramulus Mori, Bletilla striata, Radix Paeoniae Rubra, Rhizoma Atractylodis, Asarum sieboldi, Herba Leonuri, Radix Ginseng Rubra and Radix Bupleuri as the raw materials, with reasonable compatibility. By controlling the amount of each medical material, and by improving the preparation method, particularly by controlling the amount of added clear water and the decocting time, the prepared external-use curing traditional Chinese medicine has extraordinary efficacy of promoting blood circulation and removing blood stasis, relieving rigidity of muscles and itching, consolidating kidney and strengthening spleen, and balancing the function of zang-fu viscera, achieving the purpose of eliminating the focus from internal of the human body.

The external-use nursing traditional Chinese medicine of the present invention uses Rehmannia glutinosa Libosch, Rehmannia glutinosa, Paeonia suffruticosa Andr., Alisma plantago aquatica, Ophiopogon japonicus, aloes, Astragalus membranaceus, Poria cocos, FRUCTUS CORNI, Rhizoma Dioscoreae, peach kernel, tremella and Panax as the raw materials, with reasonable compatibility. By controlling the amount of each medical material, and by improving the preparation method, particularly by controlling the meshes of the ground medical materials, and the ratio of the added vaseline and honey, the prepared external-use nursing traditional Chinese medicine is in form of paste, and has super efficacy of continuously fostering the skin cell, and comprehensively repairing skin defects such as skin lines, drying and chapping and skin types being too stiff. The external-use nursing paste has moderate viscosity and softness, and is easy to be absorbed, dramatically increasing the therapeutic effect.

The external-use curing traditional Chinese medicine and the external-use nursing traditional Chinese medicine of the present invention are used in conjunction, and have features of inner and outer concurrently therapy and treating the disease in both the principal and secondary aspects, and can radically solve problems of recurrence of ichthyosis, achieving the purpose of long term cure. The external-use traditional Chinese medicine is suitable for all types of ichthyosis patients and population with severe drying skin, always used externally and convenient in use, the patients free of pain, without side effect, and anti-medicine reaction is not produced in the patent's body, and it operates quickly and has significantly therapeutic effect.

DETAILED DESCRIPTION OF THE PREFERRED EMBODIMENTS

Embodiment 1

Figure 1:
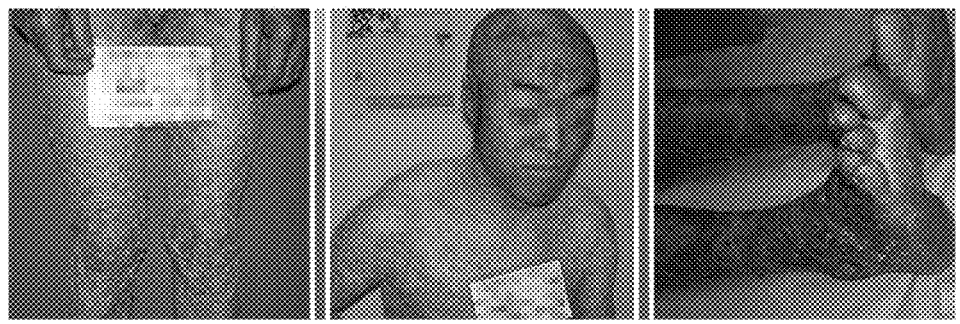
FIG. 1 is a pre-therapy photo of a patient before using the external-use traditional Chinese medicine of the present invention in Case 1.

(1) Various medical materials are weighed in the following proportions, and mixed to obtain medical material mixture of external-use curing traditional Chinese medicine: 6 g of Cortex Dictamni, 5 g of Herba Lycopodii, 3 g of Flos Carthami, 3 g of Herba speranskiae tuberculatae, 6 g of Herba Menthae, 4 g of Folium Artemisiae of Argyi, 3 g of GONGGUI, 3 g of Fructus Kochiae, 3 g of Cortex erythrinae, 3 g of Herba Artemisiae, 3 g of Ramulus Mori, 3 g of Bletilla striata, 3 g of Radix Paeoniae Rubra, 3 g of Rhizoma Atractylodis, 3 g of Asarum sieboldi, 2 g of Herba Leonuri, 3 g of Radix Ginseng Rubra and 4 g of Radix Bupleuri;

(2) The medical material mixture of external-use curing traditional Chinese medicine is packed into an organza bag to obtain a medicine package.

Embodiment 2

(1) Various medical materials are weighed in the following proportions, and mixed to obtain medical material mixture of external-use curing traditional Chinese medicine: 10 g of Cortex Dictamni, 8 g of Herba Lycopodii, 8 g of Flos Carthami, 8 g of Herba speranskiae tuberculatae, 10 g of Herba Menthae, 8 g of Folium Artemisiae Argyi, 6 g of GONGGUI, 6 g of Fructus Kochiae, 6 g of Cortex erythrinae, 6 g of Herba Artemisiae, 6 g of Ramulus Mori, 6 g of Bletilla striata, 8 g of Radix Paeoniae Rubra, 6 g of Rhizoma Atractylodis, 6 g of Asarum sieboldi, 4 g of Herba Leonuri, 5 g of Radix Ginseng Rubra and 8 g of Radix Bupleuri;

(2) the medical material mixture of external-use curing traditional Chinese medicine is packed into an organza bag to obtain a medicine package.

Embodiment 3

(1) Various medical materials are weighed in the following proportions, and mixed to obtain medical material mixture of external-use curing traditional Chinese medicine: 7 g of Cortex Dictamni, 6 g of Herba Lycopodii, 4 g of Flos Carthami, 4 g of Herba speranskiae tuberculatae, 7 g of Herba Menthae, 5 g of Folium Artemisiae Argyi, 4 g of GONGGUI, 4 g of Fructus Kochiae, 4 g of Cortex erythrinae, 4 g of Herba Artemisiae, 4 g of Ramulus Mori, 4 g of Bletilla striata, 4 g of Radix Paeoniae Rubra, 4 g of Rhizoma Atractylodis, 5 g of Asarum sieboldi, 3 g of Herba Leonuri, 4 g of Radix Ginseng Rubra and 5 g of Radix Bupleuri;

(2) the medical material mixture of external-use curing traditional Chinese medicine is packed into an organza bag to obtain a medicine package.

Embodiment 4

(1) Various medical materials are weighed in the following proportions, and mixed to obtain medical material mixture of external-use curing traditional Chinese medicine: 9 g of Cortex Dictamni, 7 g of Herba Lycopodii, 6 g of Flos Carthami, 7 g of Herba speranskiae tuberculatae, 9 g of Herba Menthae, 7 g of Folium Artemisiae Argyi, 5 g of GONGGUI, 5 g of Fructus Kochiae, 5 g of Cortex erythrinae, 5 g of Herba Artemisiae, 6 g of Ramulus Mori, 5 g of Bletilla striata, 7 g of Radix Paeoniae Rubra, 5 g of Rhizoma Atractylodis, 6 g of Asarum sieboldi, 4 g of Herba Leonuri, 5 g of Radix Ginseng Rubra and 7 g of Radix Bupleuri;

(2) the medical material mixture of external-use curing traditional Chinese medicine is packed into an organza bag to obtain a medicine package.

Embodiment 5

(1) Various medical materials are weighed in the following proportions, and mixed to obtain medical material mixture of external-use curing traditional Chinese medicine: 10 g of Cortex Dictamni, 6 g of Herba Lycopodii, 5 g of Flos Carthami, 5 g of Herba speranskiae tuberculatae, 6 g of Herba Menthae, 8 g of Folium Artemisiae Argyi, 4 g of GONGGUI, 6 g of Fructus Kochiae, 6 g of Cortex erythrinae, 7 g of Herba Artemisiae, 6 g of Ramulus Mori, 5 g of Bletilla striata, 8 g of Radix Paeoniae Rubra, 5 g of Rhizoma Atractylodis, 4 g of Asarum sieboldi, 2 g of Herba Leonuri, 4 g of Radix Ginseng Rubra and 6 g of Radix Bupleuri;

(2) The medical material mixture of external-use curing traditional Chinese medicine is packed into an organza bag to obtain a medicine package.

Embodiment 6

(1) Various medical materials are weighed in the following proportions, and mixed to obtain medical material mixture of external-use curing traditional Chinese medicine: 6 g of Cortex Dictamni, 5 g of Herba Lycopodii, 3 g of Flos Carthami, 3 g of Herba speranskiae tuberculatae, 6 g of Herba Menthae, 4 g of Folium Artemisiae Argyi, 3 g of GONGGUI, 3 g of Fructus Kochiae, 3 g of Cortex erythrinae, 3 g of Herba Artemisiae, 3 g of Ramulus Mori, 3 g of Bletilla striata, 3 g of Radix Paeoniae Rubra, 3 g of Rhizoma Atractylodis, 3 g of Asarum sieboldi, 2 g of Herba Leonuri, 3 g of Radix Ginseng Rubra and 4 g of Radix Bupleuri;

(2) after adding 25 L clear water into the medical material mixture of external-use curing traditional Chinese medicine, firstly it is boiled with high heat, and then decocted for 20 minutes with slow fire;

(3) it is filtered to obtain liquid medicine.

Embodiment 7

(1) Various medical materials are weighed in the following proportions, and mixed to obtain medical material mixture of external-use curing traditional Chinese medicine: 10 g of Cortex Dictamni, 8 g of Herba Lycopodii, 8 g of Flos Carthami, 8 g of Herba speranskiae tuberculatae, 10 g of Herba Menthae, 8 g of Folium Artemisiae Argyi, 6 g of GONGGUI, 6 g of Fructus Kochiae, 6 g of Cortex erythrinae, 6 g of Herba Artemisiae, 6 g of Ramulus Mori, 6 g of Bletilla striata, 8 g of Radix Paeoniae Rubra, 6 g of Rhizoma Atractylodis, 6 g of Asarum sieboldi, 4 g of Herba Leonuri, 5 g of Radix Ginseng Rubra and 8 g of Radix Bupleuri;

(2) after adding 35 L clear water into the medical material mixture of external-use curing traditional Chinese medicine, firstly it is boiled with high heat, and then decocted for 40 minutes with slow fire;

(3) it is filtered to obtain liquid medicine.

Embodiment 8

(1) Various medical materials are weighed in the following proportions, and mixed to obtain medical material mixture of external-use curing traditional Chinese medicine: 7 g of Cortex Dictamni, 6 g of Herba Lycopodii, 4 g of Flos Carthami, 4 g of Herba speranskiae tuberculatae, 7 g of Herba Menthae, 5 g of Folium Artemisiae Argyi, 4 g of GONGGUI, 4 g of Fructus Kochiae, 4 g of Cortex erythrinae, 4 g of Herba Artemisiae, 4 g of Ramulus Mori, 4 g of Bletilla striata, 4 g of Radix Paeoniae Rubra, 4 g of Rhizoma Atractylodis, 5 g of Asarum sieboldi, 3 g of Herba Leonuri, 4 g of Radix Ginseng Rubra and 5 g of Radix Bupleuri;

(2) after adding 28 L clear water into the medical material mixture of external-use curing traditional Chinese medicine, firstly it is boiled with high heat, and then decocted for 25 minutes with slow fire;

(3) it is filtered to obtain liquid medicine.

Embodiment 9

(1) Various medical materials are weighed in the following proportions, and mixed to obtain medical material mixture of external-use curing traditional Chinese medicine: 9 g of Cortex Dictamni, 7 g of Herba Lycopodii, 6 g of Flos Carthami, 7 g of Herba speranskiae tuberculatae, 9 g of Herba Menthae, 7 g of Folium Artemisiae Argyi, 5 g of GONGGUI, 5 g of Fructus Kochiae, 5 g of Cortex erythrinae, 5 g of Herba Artemisiae, 6 g of Ramulus Mori, 5 g of Bletilla striata, 7 g of Radix Paeoniae Rubra, 5 g of Rhizoma Atractylodis, 6 g of Asarum sieboldi, 4 of Herba Leonuri, 5 g of Radix Ginseng Rubra and 7 g of Radix Bupleuri;

(2) after adding 32 L clear water into the medical material mixture of external-use curing traditional Chinese medicine, firstly it is boiled with high heat, and then decocted for 35 minutes with slow fire;

(3) it is filtered to obtain liquid medicine.

Embodiment 10

(1) Various medical materials are weighed in the following proportions, and mixed to obtain medical material mixture of external-use curing traditional Chinese medicine: 8 g of Cortex Dictamni, 7 g of Herba Lycopodii, 5 g of Flos Carthami, 6 g of Herba speranskiae tuberculatae, 8 g of Herba Menthae, 6 g of Folium Artemisiae Argyi, 5 g of GONGGUI, 5 g of Fructus Kochiae, 5 g of Cortex erythrinae, 5 g of Herba Artemisiae, 5 g of Ramulus Mori, 5 g of Bletilla striata, 6 g of Radix Paeoniae Rubra, 5 g of Rhizoma Atractylodis, 6 g of Asarum sieboldi, 4 g of Herba Leonuri, 5 g of Radix Ginseng Rubra and 6 g of Radix Bupleuri;

(2) after adding 30 L clear water into the medical material mixture of external-use curing traditional Chinese medicine, firstly it is boiled with high heat, and then decocted for 30 minutes with slow fire;

(3) it is filtered to obtain liquid medicine.

Embodiment 11

(1) Various medical materials are weighed in the following proportions, and mixed to obtain medical material mixture of external-use curing traditional Chinese medicine: 6 g of Cortex Dictamni, 6 g of Herba Lycopodii, 3 g of Flos Carthami, 3 g of Herba speranskiae tuberculatae, 4 g of Herba Menthae, 8 g of Folium Artemisiae Argyi, 6 g of GONGGUI, 4 g of Fructus Kochiae, 6 g of Cortex erythrinae, 3 g of Herba Artemisiae, 6 g of Ramulus Mori, 6 g of Bletilla striata, 8 g of Radix Paeoniae Rubra, 3 g of Rhizoma Atractylodis, 3 g of Asarum sieboldi, 2 g of Herba Leonuri, 3 g of Radix Ginseng Rubra and 6 g of Radix Bupleuri;

(2) after adding 30 L clear water into the medical material mixture of external-use curing traditional Chinese medicine, firstly it is boiled with high heat, and then decocted for 30 minutes with slow fire;

(3) it is filtered to obtain liquid medicine.

Embodiment 12

(1) Various medical materials are weighed in the following proportions, and mixed to obtain medical material mixture of external-use nursing traditional Chinese medicine: 3 g of Rehmannia glutinosa Libosch, 3 g of Rehmannia glutinosa, 3 g of Paeonia suffruticosa Andr., 3 g of Alisma plantago aquatica, 3 g of Ophiopogon japonicus, 3 g of aloes, 10 g of Astragalus membranaceus, 3 g of Poria cocos, 5 g of FRUCTUS CORNI, 5 g of Rhizoma Dioscoreae, 3 g of peach kernel, 3 g of tremella and 1 g of Panax;

(2) the medical material mixture is ground and pass through a sieve with 100 meshes to obtain product.

Embodiment 13

(1) Various medical materials are weighed in the following proportions, and mixed to obtain medical material mixture of external-use nursing traditional Chinese medicine: 6 g of Rehmannia glutinosa Libosch, 6 g of Rehmannia glutinosa, 6 g of Paeonia suffruticosa Andr., 5 g of Alisma plantago aquatica, 8 g of Ophiopogon japonicus, 8 g of aloes, 30 g of Astragalus membranaceus, 5 g of Poria cocos, 14 g of FRUCTUS CORNI, 14 g of Rhizoma Dioscoreae, 6 g of peach kernel, 6 g of tremella and 3 g of Panax;

(2) the medical material mixture is ground and passes through a sieve with 140 meshes to obtain the product.

Embodiment 14

(1) Various medical materials are weighed in the following proportions, and mixed to obtain medical material mixture of external-use nursing traditional Chinese medicine: 4 g of Rehmannia glutinosa Libosch, 4 g of Rehmannia glutinosa, 4 g of Paeonia suffruticosa Andr., 4 g of Alisma plantago aquatica, 4 g of Ophiopogon japonicus, 4 g of aloes, 15 g of Astragalus membranaceus, 4 g of Poria cocos, 7 g of FRUCTUS CORNI, 8 g of Rhizoma Dioscoreae, 4 g of peach kernel, 4 g of tremella and 2 g of Panax;

(2) the medical material mixture is ground and passes through a sieve with 120 meshes to obtain the product.

Embodiment 15

(1) Various medical materials are weighed in the following proportions, and mixed to obtain medical material mixture of external-use nursing traditional Chinese medicine: 5 g of Rehmannia glutinosa Libosch, 5 g of Rehmannia glutinosa, 5 g of Paeonia suffruticosa Andr., 5 g of Alisma plantago aquatica, 7 g of Ophiopogon japonicus, 7 g of aloes, 25 g of Astragalus membranaceus, 5 g of Poria cocos, 12 g of FRUCTUS CORNI, 12 g of Rhizoma Dioscoreae, 5 g of peach kernel, 5 g of tremella and 3 g of Panax;

(2) the medical material mixture is ground and passes through a sieve with 120 meshes to obtain the product.

Embodiment 16

(1) Various medical materials are weighed in the following proportions, and mixed to obtain medical material mixture of external-use nursing traditional Chinese medicine: 12 g of Rehmannia glutinosa Libosch, 12 g of Rehmannia glutinosa, 8 g of Paeonia suffruticosa Andr., 5 g of Alisma plantago aquatica, 15 g of Ophiopogon japonicus, 12 g of aloes, 40 g of Astragalus membranaceus, 6 g of Poria cocos, 15 g of FRUCTUS CORNI, 16 g of Rhizoma Dioscoreae, 12 g of peach kernel, 8 g of tremella and 6 g of Panax;

(2) the medical material mixture is ground and passes through a sieve with 120 meshes to obtain the product.

Embodiment 17

(1) Various medical materials are weighed in the following proportions, and mixed to obtain medical material mixture of external-use nursing traditional Chinese medicine: 6 g of Rehmannia glutinosa Libosch, 6 g of Rehmannia glutinosa, 8 g of Paeonia suffruticosa Andr., 6 g of Alisma plantago aquatica, 12 g of Ophiopogon japonicus, 16 g of aloes, 30 g of Astragalus membranaceus, 10 g of Poria cocos, 16 g of FRUCTUS CORNI, 20 g of Rhizoma Dioscoreae, 12 g of peach kernel, 10 g of tremella and 3 g of Panax;

(2) the medical material mixture is ground and passes through a sieve with 120 meshes to obtain the product.

Embodiment 18

Vaseline and honey are added into the product of Embodiment 12, and mixed well to form nursing paste, and mass ratio of the product of Embodiment 12, the vaseline and the honey is 2:0.5:0.5.

Embodiment 19

Vaseline and honey are added into the product of Embodiment 13, and mixed well to form nursing paste, and mass ratio of the product of Embodiment 13, the vaseline and the honey is 3:1.5:1.5.

Embodiment 20

Vaseline and honey are added into the product of Embodiment 14, and mixed well to form nursing paste, and mass ratio of the product of Embodiment 14, the vaseline and the honey is 2:1:1.

Embodiment 21

Vaseline and honey are added into the product of Embodiment 15, and mixed well to form nursing paste, and mass ratio of the product of Embodiment 15, the vaseline and the honey is 2:1:1.

Embodiment 22

Vaseline and honey are added into the product of Embodiment 16, and mixed well to form nursing paste, and mass ratio of the product of Embodiment 16, the vaseline and the honey is 2:1:1.

Embodiment 23

Vaseline and honey are added into the product of Embodiment 17, and mixed well to form nursing paste, and mass ratio of the product of Embodiment 17, the vaseline and the honey is 2:1:1.

Hereinafter, specific cases will be given to illustrate that the external-use traditional Chinese medicine prepared according to the method provided by present invention has extraordinary efficacy of healing ichthyosis and xerodermia and is able to effectively prevent recurrence.

Case 1: Patient Wang, from Xinjiang province, male, 21 years old. Illness state of the patient was comparatively severe, with brown quadrangle scales spread all over the whole body, and hair lost off the entire head, and there appears the symptom of eyelid eversion, it looks as if the whole body was wrapped with white yarn, and thick horniness presents at joints and was darker compared with scales in other positions of the body, as shown in FIG. 1. Duration of this patient's disease is longer, and normally the treatment only relies on applying hormone medicinal ointment, but as along with the disease aggravated, the effect of applying hormone medicinal ointment is not obvious, and along with the scales increasing, considerable trouble is caused to the patient's life. If the illness continuously develops, the symptom will be further exacerbated, and extremity' function of the patient will be even affected.

Therapy method used to the patient is fumigation and steaming therapy. Fumigation and steaming therapy can make various active ingredients in the medical materials infiltrate layer by layer. The medical materials are warmed to form traditional Chinese medicine steam, with heat, humidity and potency of drug integrated, and penetrate into meridian and collateral, QI and blood and zang-fu viscera via body surface, aperture and acupoint. Therapy method can quickly remove horniness casued by keratinization of skin epidermis and assist in opening sweat glands, strengthening metabolism and absorption function of the skin, so as to obtain efficacy of clearing heat and detoxicating, promoting blood circulation and removing blood stasis, relieving rigidity of muscles and activating collaterals and balancing the function of zang-fu viscera, and ultimately eliminate the focus.

Figure 2:
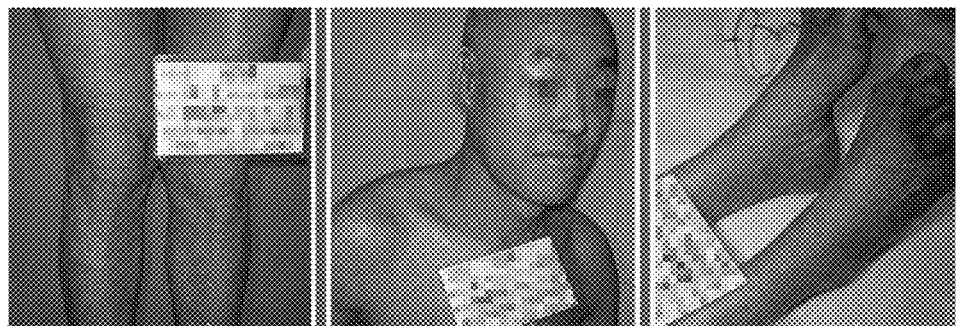
FIG. 2 is a post-therapy photo of the patient after using the external-use traditional Chinese medicine of the present invention in Case 1.

The specific steps are as follows: putting the product of Embodiment 5 of the present invention into a fumigation and steaming box which produces medicine steam acting on baring skin of the whole body (head remains outside the fumigation and steaming box). Fumigation and steaming therapy is made once a day, for 40 minutes per time at fumigating temperature of 37. Scales of the skin begin to peel off since the 7th day. After each fumigation and steaming therapy, the diseased sites are evenly applied with the nursing paste of Embodiment 22, and massaged for 2-3 minutes, and then rinsed after 2 hours. The scales of skin peel off almost entirely at the 20th time. In order to obtain the efficacy of promoting blood circulation and removing blood stasis, fostering the skin, and relieving rigidity of muscles and itching, the therapy is continuously made until the $30^{th}$ time and the skin substantially recovers to normal. During the usage of the external-use traditional Chinese medicine, the body does not feel any debilitation, without anti-medicine reaction and side effect. Doctor's advice is to apply the nursing paste every day, and the patient's skin is kept moistened so far, no longer dry, without scales generated and recurrence, as shown in FIG. 2.

Figure 3:
FIG. 3 is a pre-therapy photo of a patient before using the external-use traditional Chinese medicine of the present invention in Case 2.

Case 2: patient Wang, from Sichuan province, male, 7 years old. The age of this patient was younger. Skin damages occurred at birth, thick scales covered over the whole body and spread throughout the whole body surface, as if the whole body were coated by a layer of armor. The scales are quadrangle, in color of chocolate brown. The patient's palmoplantar keratoderma was severe, and could not normally perspire, severely affecting functions of hands and feet and involving the head, and alopecia phenomenon severe, which cause considerable effects to the patient's life, and brought heavy psychological burden, as shown in FIG. 3. The patient took oral traditional Chinese medicine for a long term, but since the illness of the patient was comparatively severe, the traditional Chinese medicine operates slowly, and considering this patient was quite young, taking medicine for a long term would bring side effect to the body. It is best to adopt a healthy therapy as early as possible, to allow the patient to have healthy life sooner.

Figure 4:
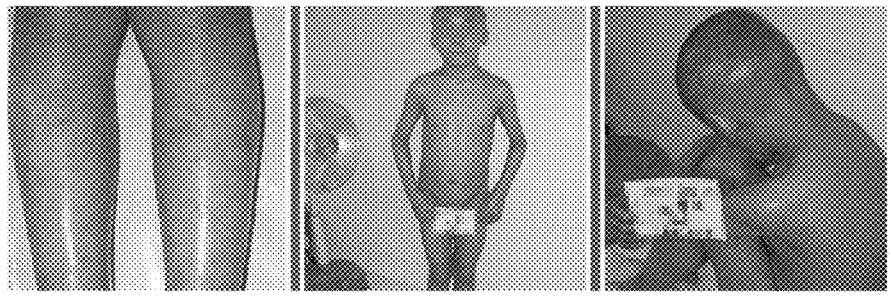
FIG. 4 is a post-therapy photo of the patient after using the external-use traditional Chinese medicine of the present invention in Case 2.

The therapy method used to the patient is a soaking and washing therapy. The specific steps are as follows: pouring the product of Embodiment 11 into a soaking and washing container, adjusting the temperature to 30-35° C. with clear water, covering the container with a thin film to slow down the falling speed of the temperature, making his head remain outside, and the patient being soaked for 30-35 minutes. If the temperature is too low, 20 L of clear water can be added into the raw medical residues again, and it is decoctied for 20 minutes, and then blended into the soaking and washing container. The soaking and washing therapy is made once a day. Scales of the skin begin to peel off since the 10th day. After each soaking and washing therapy, the diseased sites are evenly applied with the nursing paste of Embodiment 23, massaged for 2-3 minutes and then rinsed after 2 hours. The scales of skin peel off almost entirely at the 20th time. In order to obtain efficacy of promoting blood circulation and removing blood stasis, fostering the skin, and relieving rigidity of muscles and itching, the therapy is continuously made until the $30^{th}$ time, and the skin substantially recovers to normal. During the usage of the external-use traditional Chinese medicine, the body does not have any anti-medicine reaction, without side effect. Doctor's advice is to apply the nursing paste every day, and the patient's skin remains moistened so far, no longer dry, without scales generated and recurrence, as shown in FIG. 4.

It can be seen from the above cases that the external-use traditional Chinese medicine of the present invention is suitable for all types of ichthyosis patients and population with severe drying skin, operating quickly, the patients free of pain, without side effect, and the body does not produce anti-medicine reaction, with significantly therapeutic effect. The external-use traditional Chinese medicine can thoroughly cure ichthyosis and severe drying skin, with less recurrence.

The foregoing are only the preferred embodiments of the present invention, without limiting the present invention. For one skilled in the art, the present invention can have various modifications and variations. Within the spirit and principle of the present invention, any modification, equal replacement, improvement etc. should be included in the protection scope of the present invention.

What is claimed is:

1. External-use traditional Chinese medicine for ichthyosis and xerodermia characterized by comprising external-use curing traditional Chinese medicine and external-use nursing traditional Chinese medicine, wherein parts by weight are as follows:

raw materials of the external-use curing traditional Chinese medicine comprises: Cortex Dictamni in 6-10 parts, Herba Lycopodii 5-8 in parts, Flos Carthami in 3-8 parts, Herba speranskiae tuberculatae in 3-8 parts, Herba Menthae in 6-10 parts, Folium Artemisiae Argyi in 4-8 parts, Guan Gui in 3-6 parts, Fructus Kochiae in 3-6 parts, Cortex erythrinae in 3-6 parts, Herba Artemisiae in 3-6 parts, Ramulus Mori in 3-6 parts, Bletilla striata in 3-6 parts, Radix Paeoniae Rubra in 3-8 parts, Rhizoma Atractylodis in 3-6 parts, Asarum sieboldi in 3-6 parts, Herba Leonuri in 2-4 parts, Radix Ginseng Rubra in 3-5 parts, and Radix Bupleuri in 4-8 parts; and raw materials of the external-use nursing traditional Chinese medicine comprising: Rehmannia glutinosa Libosch in 3-6 parts, Rehmannia glutinosa in 3-6 parts, Paeonia suffruticosa in 3-6 parts, Alisma plantago aquatica in 3-5 parts, Ophiopogon japonicus in 3-8 parts, aloes in 3-8 parts, Astragalus membranaceus in 10-30 parts, Poria cocos in 3-5 parts, FRUCTUS CORNI in 5-14 parts, Rhizoma Dioscoreae in 5-14 parts, peach kernel in 3-6 parts, tremella in 3-6 parts, and Panax in 1-3 parts.

2. The external-use traditional Chinese medicine for ichthyosis and xerodermia according to claim 1, characterized in that the raw materials of the external-use curing traditional Chinese medicine comprise: Cortex Dictamni in 7-9 parts, Herba Lycopodii 6-7 in parts, Flos Carthami in 4-6 parts, Herba speranskiae tuberculatae in 4-7 parts, Herba Menthae in 7-9 parts, Folium Artemisiae Argyi in 5-7 parts, Guan Gui in 4-5 parts, Fructus Kochiae in 4-5 parts, Cortex erythrinae in 4-5 parts, Herba Artemisiae in 4-5 parts, Ramulus Mori in 4-6 parts, Bletilla striata in 4-5 parts, Radix Paeoniae Rubra in 4-7 parts, Rhizoma Atractylodis in 4-5 parts, Asarum sieboldi in 5-6 parts, Herba Leonuri in 3-4 parts, Radix Ginseng Rubra in 4-5 parts, and Radix Bupleuri in 5-7 parts.

3. The external-use traditional Chinese medicine for ichthyosis and xerodermia according to claim 1, characterized in that the raw materials of the external-use nursing traditional Chinese medicine comprise: Rehmannia glutinosa Libosch in 4-5 parts, Rehmannia glutinosa in 4-5 parts, Paeonia suffruticosa in 4-5 parts, Alisma plantago aquatica in 4-5 parts, Ophiopogon japonicus in 4-7 parts, aloes in 4-7 parts, Astragalus membranaceus in 15-25 parts, Poria cocos in 4-5 parts, FRUCTUS CORNI in 7-12 parts, Rhizoma Dioscoreae in 8-12 parts, peach kernel in 4-5 parts, tremella in 4-5 parts, and Panax in 2-3 parts.

4. A preparation method of the external-use traditional Chinese medicine for ichthyosis and xerodermia according to claim 1 characterized by comprising a preparation method of the external-use curing traditional Chinese medicine and a preparation method of the external-use nursing traditional Chinese medicine, wherein the preparation method of the external-use curing traditional Chinese medicine comprises the following steps: mixing the raw materials of the external-use curing traditional Chinese medicine and packing it into an organza bag to obtain a medicine package; or the preparation method of the external-use curing traditional Chinese medicine comprises the following steps:

(1) mixing the raw materials of the external-use curing traditional Chinese medicine;

(2) adding 25-35 L clear water, and afterwards, firstly boiling it with high heat, then decocting it for 20-40 minutes with slow fire; and (3) filtering it to obtain liquid medicine; and the preparation method of the external-use nursing traditional Chinese medicine comprises the following steps: mixing and grinding the raw materials of the external-use nursing traditional Chinese medicine, then pass it through a sieve with 100-140 meshes to obtain a product.

5. The preparation method of the external-use traditional Chinese medicine used for ichthyosis and xerodermia according to claim 4, characterized in that in the preparation method of the external-use nursing traditional Chinese medicine, the raw materials of the external-use nursing traditional Chinese medicine pass through a sieve with 120 meshes after being mixed and ground.

6. The preparation method of the external-use traditional Chinese medicine used for ichthyosis and xerodermia according to claim 4, characterized in that in the step (2) of the preparation method of the external-use curing traditional Chinese medicine, the volume of the added clear water is 30 L.

7. The preparation method of the external-use traditional Chinese medicine used for ichthyosis and xerodermia according to claim 4, characterized in that in the step (2) of the preparation method of the external-use curing traditional Chinese medicine, the decocting duration is 25-35 minutes.

8. The preparation method of the external-use traditional Chinese medicine used for ichthyosis and xerodermia according to claim 7, characterized in that in the step (2) of the preparation method of the external-use curing traditional Chinese medicine, the decocting duration is 30 minutes.

9. The preparation method of the external-use traditional Chinese medicine used for ichthyosis and xerodermia according to claim 4, characterized in that vaseline and honey are added into the external-use nursing traditional Chinese medicine, and mixed well to form nursing paste, wherein mass ratio of the external-use nursing traditional Chinese medicine, the vaseline and the honey is 2-3:0.5-1.5:0.5-1.5.

10. The preparation method of the external-use traditional Chinese medicine for for ichthyosis and xerodermia according to claim 9, characterized in that the mass ratio of the external-use nursing traditional Chinese medicine, the vaseline and the honey is 2:1:1.

11. A preparation method of the external-use traditional Chinese medicine for for ichthyosis and xerodermia according to claim 2 characterized by comprising a preparation method of the external-use curing traditional Chinese medicine and a preparation method of the external-use nursing traditional Chinese medicine, wherein the preparation method of the external-use curing traditional Chinese medicine comprises the following steps: mixing the raw materials of the external-use curing traditional Chinese medicine and packing it into an organza bag to obtain a medicine package; or the preparation method of the external-use curing traditional Chinese medicine comprises the following steps:

(1) mixing the raw materials of the external-use curing traditional Chinese medicine;

(2) adding 25-35 L clear water, and afterwards, firstly boiling it with high heat, then decocting it for 20-40 minutes with slow fire; and (3) filtering it to obtain liquid medicine; and the preparation method of the external-use nursing traditional Chinese medicine comprises the following steps: mixing and grinding the raw materials of the external-use nursing traditional Chinese medicine, then pass it through a sieve with 100-140 meshes to obtain a product.

12. The preparation method of the external-use traditional Chinese medicine used for ichthyosis and xerodermia according to claim 11, characterized in that in the preparation method of the external-use nursing traditional Chinese medicine, the raw materials of the external-use nursing traditional Chinese medicine pass through a sieve with 120 meshes after being mixed and ground.

13. The preparation method of the external-use traditional Chinese medicine used for ichthyosis and xerodermia according to claim 11, characterized in that in the step (2) of the preparation method of the external-use curing traditional Chinese medicine, the volume of the added clear water is 30 L.

14. The preparation method of the external-use traditional Chinese medicine used for ichthyosis and xerodermia according to claim 11, characterized in that in the step (2) of the preparation method of the external-use curing traditional Chinese medicine, the decocting duration is 25-35 minutes.

15. The preparation method of the external-use traditional Chinese medicine used for ichthyosis and xerodermia according to claim 14, characterized in that in the step (2) of the preparation method of the external-use curing traditional Chinese medicine, the decocting duration is 30 minutes.

16. The preparation method of the external-use traditional Chinese medicine used for ichthyosis and xerodermia according to claim 11, characterized in that vaseline and honey are added into the external-use nursing traditional Chinese medicine, and mixed well to form nursing paste, wherein mass ratio of the external-use nursing traditional Chinese medicine, the vaseline and the honey is 2-3:0.5-1.5:0.5-1.5.

17. The preparation method of the external-use traditional Chinese medicine for for ichthyosis and xerodermia according to claim 16, characterized in that the mass ratio of the external-use nursing traditional Chinese medicine, the vaseline and the honey is 2:1:1.

18. A preparation method of the external-use traditional Chinese medicine for for ichthyosis and xerodermia according to claim 3 characterized by comprising a preparation method of the external-use curing traditional Chinese medicine and a preparation method of the external-use nursing traditional Chinese medicine, wherein
the preparation method of the external-use curing traditional Chinese medicine comprises the following steps:
mixing the raw materials of the external-use curing traditional Chinese medicine and packing it into an organza bag to obtain a medicine package; or
the preparation method of the external-use curing traditional Chinese medicine comprises the following steps:
(1) mixing the raw materials of the external-use curing traditional Chinese medicine;
(2) adding 25-35 L clear water, and afterwards, firstly boiling it with high heat, then decocting it for 20-40 minutes with slow fire; and
(3) filtering it to obtain liquid medicine; and
the preparation method of the external-use nursing traditional Chinese medicine comprises the following steps: mixing and grinding the raw materials of the external-use nursing traditional Chinese medicine, then pass it through a sieve with 100-140 meshes to obtain a product.

19. The preparation method of the external-use traditional Chinese medicine used for ichthyosis and xerodermia according to claim 18, characterized in that in the preparation method of the external-use nursing traditional Chinese medicine, the raw materials of the external-use nursing traditional Chinese medicine pass through a sieve with 120 meshes after being mixed and ground.

20. The preparation method of the external-use traditional Chinese medicine used for ichthyosis and xerodermia according to claim 18, characterized in that in the step (2) of the preparation method of the external-use curing traditional Chinese medicine, the volume of the added clear water is 30 L.

21. The preparation method of the external-use traditional Chinese medicine used for ichthyosis and xerodermia according to claim 18, characterized in that in the step (2) of the preparation method of the external-use curing traditional Chinese medicine, the decocting duration is 25-35 minutes.

22. The preparation method of the external-use traditional Chinese medicine used for ichthyosis and xerodermia according to claim 21, characterized in that in the step (2) of the preparation method of the external-use curing traditional Chinese medicine, the decocting duration is 30 minutes.

23. The preparation method of the external-use traditional Chinese medicine used for ichthyosis and xerodermia according to claim 18, characterized in that vaseline and honey are added into the external-use nursing traditional Chinese medicine, and mixed well to form nursing paste, wherein mass ratio of the external-use nursing traditional Chinese medicine, the vaseline and the honey is 2-3:0.5-1.5:0.5-1.5.

24. The preparation method of the external-use traditional Chinese medicine for for ichthyosis and xerodermia according to claim 23, characterized in that the mass ratio of the external-use nursing traditional Chinese medicine, the vaseline and the honey is 2:1:1.

* * * * *